(12) United States Patent
Bolshakov et al.

(10) Patent No.: US 8,061,206 B2
(45) Date of Patent: Nov. 22, 2011

(54) CASING THICKNESS EVALUATION METHOD

(75) Inventors: Alexei Bolshakov, Pearland, TX (US); Edward J. Domangue, Houston, TX (US); Douglas J. Patterson, Spring, TX (US); Joseph G. Barolak, Spring, TX (US)

(73) Assignee: Baker Hughes Incorporated, Houston, TX (US)

( * ) Notice: Subject to any disclaimer, the term of this patent is extended or adjusted under 35 U.S.C. 154(b) by 364 days.

(21) Appl. No.: 12/426,087

(22) Filed: Apr. 17, 2009

(65) Prior Publication Data
US 2010/0263449 A1  Oct. 21, 2010

(51) Int. Cl.
*G01H 5/00* (2006.01)
(52) U.S. Cl. ............................................. 73/597
(58) Field of Classification Search ............. 73/587–597
See application file for complete search history.

(56) References Cited

U.S. PATENT DOCUMENTS

| | | | |
|---|---|---|---|
| 4,305,294 A | | 12/1981 | Vasile et al. |
| 4,556,813 A | * | 12/1985 | Baumoel ........................ 310/334 |
| 5,714,688 A | * | 2/1998 | Buttram et al. ................. 73/597 |
| 5,721,379 A | | 2/1998 | Palmer et al. |
| 6,418,796 B1 | * | 7/2002 | Baumoel ..................... 73/861.28 |
| 6,640,635 B2 | * | 11/2003 | Nakatsuka ....................... 73/643 |
| 6,850,168 B2 | | 2/2005 | Tang et al. |
| 7,675,814 B2 | * | 3/2010 | Mandal ........................... 367/35 |
| 7,773,454 B2 | * | 8/2010 | Barolak et al. ................. 367/35 |
| 2005/0190648 A1 | | 9/2005 | Tang et al. |
| 2005/0205248 A1 | | 9/2005 | Barolak et al. |
| 2005/0205268 A1 | | 9/2005 | Engels et al. |
| 2006/0198243 A1 | | 9/2006 | Tang et al. |
| 2007/0206439 A1 | | 9/2007 | Barolak et al. |
| 2007/0211572 A1 | | 9/2007 | Reiderman et al. |
| 2008/0112262 A1 | | 5/2008 | Tang et al. |
| 2008/0170467 A1 | | 7/2008 | Barolak |

OTHER PUBLICATIONS

H.J. Salzburger et al., "Thickness Measurements of Sheets and Plates with Horizontally Polarized Guided Plate Waves (SH-Modes) and Electromagnetic Ultrasonic (EMUS-) Transducers," 1987, Proceedings of 4th European Conference, p. 2314-2320, 1987.

* cited by examiner

*Primary Examiner* — Max Noori
(74) *Attorney, Agent, or Firm* — Bracewell & Giuliani LLP

(57) ABSTRACT

Evaluating casing thickness by inducing SH0 and SH1 modes of a shear wave in the casing. The SH0 group velocity and SH1 mode group velocity (Vg) are measured and the measured SH0 mode group velocity is assigned as the tubular material shear velocity (Vs). A shear wave wavelength λ from the ratio of SH0 mode frequency ($f_o$) and the measured SH0 group velocity is estimated. The tubular thickness (d) is estimated from the estimated shear wave wavelength λ. The transmitter can be calibrated to operate at an optimum frequency.

10 Claims, 10 Drawing Sheets

CASING THICKNESS EVALUATION METHOD

BACKGROUND OF THE INVENTION

1. Field of the Invention

The present disclosure relates to a device and a method for evaluating a cement bond. More specifically, the present disclosure relates to a device and method for evaluating the thickness, quality, and presence of a cement bond. Yet more specifically, the present disclosure concerns a device and method for evaluating a cement bond between cement and formation.

2. Description of Related Art

Hydrocarbon producing wellbores typically comprise casing cemented within a wellbore. Cement bonds the casing to the wellbore and is added into the annulus between the casing outer diameter and wellbore inner diameter. The cement also isolates adjacent zones within a formation from one another. Isolating adjacent zones can be important when one of the zones contains oil or gas and the other zone includes a non-hydrocarbon fluid such as water. Should the cement surrounding the casing be defective and fail to isolate the adjacent zones, water or other undesirable fluid can migrate into the hydrocarbon producing zone thus diluting or contaminating the hydrocarbons within the producing zone.

The casing is subjected to mechanical loading cycles from applied pressure differentials and thermal loading that create internal and external stresses. Corrosive substances, such as salt water and sulfur containing compounds, to name a few, can erode casing structure and reduce its yield strength. Downhole logging tools and drilling bits can damage or also erode casing. Production casing may fail due to erosion, surface damage, its loading cycles, or combinations thereof. Identifying casing defects from erosion or other damage can reveal a potential failure. Casing damage is identifiable by various measures, such as by evaluating casing thickness. Examples of casing analysis devices include acoustic measurement tools, magnetic flux leakage apparatus; eddy current devices; and mechanical calipers.

BRIEF SUMMARY OF THE INVENTION

Disclosed herein is a method of evaluating a tubular used in hydrocarbon production. The method involves inserting a tool into the tubular, the tool having an electromagnetic acoustic transducer (EMAT) Optionally, the EMAT may have up to five sets of wave inducing magnetic rows, energizing the EMAT to induce a shear wave in the tubular, wherein the shear wave comprises an SH0 mode and an SH1 mode, measuring the SH0 mode group velocity, measuring the SH1 mode group velocity (Vg), assigning the measured SH0 mode group velocity as the tubular shear velocity (Vs), estimating a shear wave wavelength λ from the ratio of SH0 mode frequency ($f_o$) and the measured SH0 group velocity, and estimating the tubular thickness (d) from the estimated shear wave wavelength λ. The tubular thickness (d) may be estimated using the relationship: $d=0.5\lambda/((Vs/Vg)2-1)1/2)$. The method may further comprise a calibration step of inducing additional shear waves in the tubular over a range of frequencies, monitoring the additional shear waves' propagation in the tubular, evaluating the signal to noise ratio of monitored waves at selected frequencies, and adjusting the tool to induce shear waves at the selected frequency having the largest signal to noise ratio. Using information from the calibration step, the method may further comprise inducing a shear wave at the selected frequency having the largest signal to noise ratio, measuring the SH0 mode group velocity, and re-estimating the shear wave wavelength λ based on the measured SH0 mode group velocity. The tubular may include casing lining a wellbore or production tubing disposed in a wellbore.

DETAILED DESCRIPTION OF THE INVENTION

Figure 1:
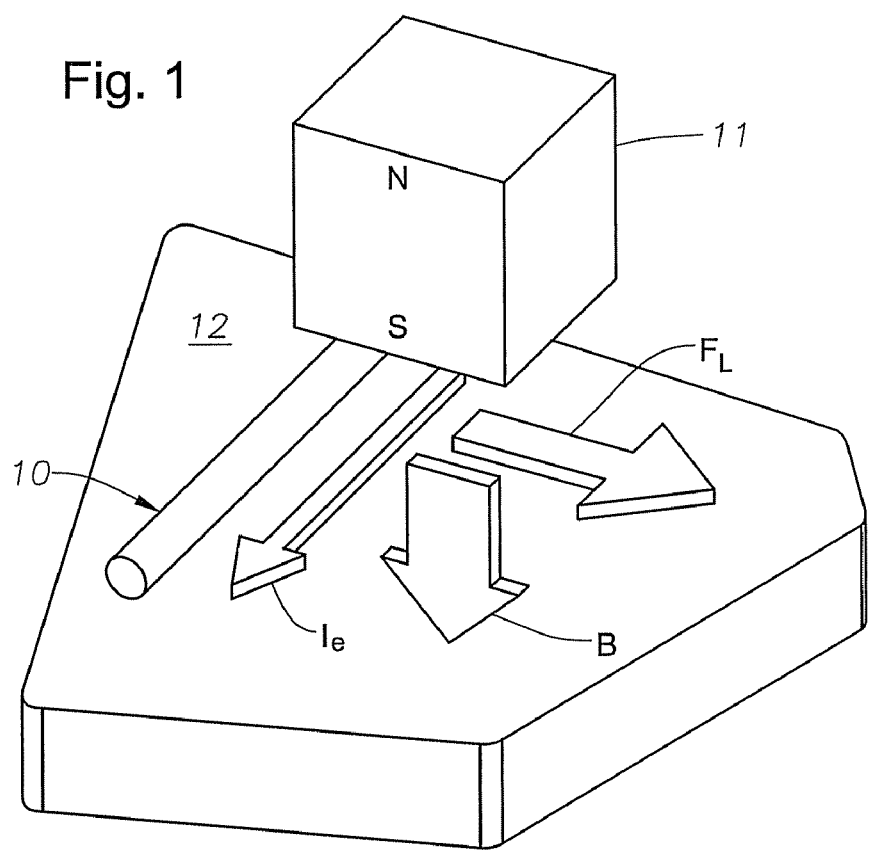
FIG. 1 schematically illustrates an embodiment of an electromagnetic acoustic transducer.

An EMAT uses non-contact electromagnetic transduction to impart physical stress to a conductive medium. With reference now to FIG. 1, a schematic example of an EMAT is provided. A current I flowing in a wire 10 positioned between a magnet 11 and a conductive surface 12 induces an equal and opposite Eddy current $I_e$ on the conductive surface 12. A Lorentz force $F_L$ can be created in the conductive surface 12 by combining a magnetic field B with the Eddy current $I_e$, where $F_L=I_e \times B$. The Lorentz force $F_L$ generates particle displacement in the conductive surface 12 creating elastic waves such as shear horizontal (SH), transversely polarized shear waves, and Lamb waves of both symmetric and asymmetric type.

Figure 2:
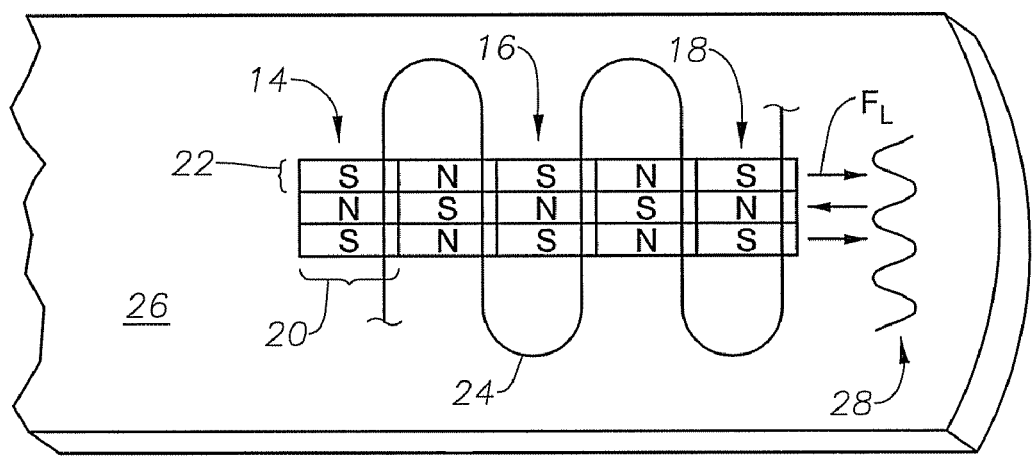
FIG. 2 is a schematic of an EMAT inducing a wave in a conductive body.

A schematic example of an EMAT 14 is provided in FIG. 2 that includes a magnetic array 16 comprising magnets 18 arranged in columns 20 and rows 22 similar to a checkerboard. A meander coil 24 extends over each column 20 changing direction with each adjacent column 20. Although the magnets 18 in each row 22 are of alternating polarity, alternating the coil 24 direction produces an additive Lorentz force $F_L$ in a single direction. Moreover, as illustrated in FIG. 2, alternating magnet 18 polarity along each column 20 creates oppositely oriented Lorentz forces $F_L$ in adjacent rows 22. As noted above, the Lorentz forces $F_L$ displace particles on the conductive surface 26 to induce a wave 28 in a body 30 being analyzed. In one example, the body 30 comprises a section of a downhole tubular, such as casing bonded in a borehole or production tubing.

Figure 3:
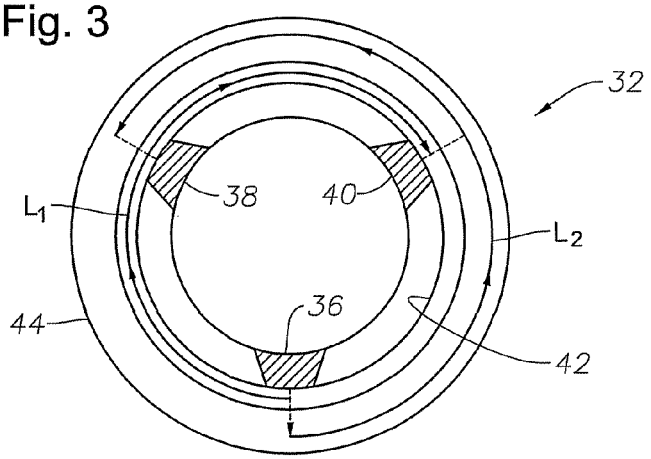
FIG. 3 is a cross sectional view of a downhole tool having acoustic transducers, the tool disposed in casing.

FIG. 3 depicts a sectional schematic view of an example of a logging tool 32. The logging tool 32 comprises a cylindrical body 34 having transducers arranged along the body 34. In this example, the transducers include a transmitter 36 and a pair of receivers 38, 40 where the receivers 38, 40 are disposed on the body 34 outer circumference each about 120° from the transmitter 36. The transducers (36, 38, 40) can be an EMAT, a piezoelectric transducer, or a wedge type transducer. As shown, an acoustic signal generated at the transmitter 36, travels to the receiver 38 as illustrated by line $L_1$ (clockwise) and to receiver 40 as illustrated by line $L_2$ (counterclockwise). The signal's frequency content and group velocities can be analyzed to estimate local properties (such as shear velocity) and thickness of a casing or other downhole tubular.

Equations modeling two-dimensional SH wave propagation in the layered media include:

$$f_n = V_s \times \sqrt{1 + (0.5\lambda n/d)^2}/\lambda; \quad (1)$$

$$V_p^n = V_s \times \sqrt{1 + (0.5\lambda n/d)^2}; \quad (2)$$

$$V_g^n = V_s / \sqrt{1 + (0.5\lambda n/d)^2}; \quad (3).$$

n is the SH mode order ($n \geq 0$), d is plate thickness, $\lambda$ is the shear wave wavelength, $V_s$ is the material shear velocity, and $f_n$, $V_p^n$, and $V_g^n$ respectively represent the nth SH mode frequency, phase, and group velocity. B. A. Auld, 1990, Acoustic Fields and Waves in Solids, Robert E. Krieger Publishing Company, Inc, Malabar, Fla., p. 74-76.

Based on equations (1)-(3) the SH0 mode group and phase velocities equal the material shear velocity. Also, the $0^{th}$ mode frequency equals the ratio of material shear velocity and wavelength:

$$f_0 = V_s/\lambda, \; V_p^0 = V_g^0 = V_s. \quad (4)$$

Therefore, measuring SH0 mode group or phase velocity yields the material shear velocity $V_s$.

Applying the above relationships to wellbore tubular evaluation, such as acoustically logging a casing, values for group velocity, phase velocity and frequency are attainable. For example, a tool having an acoustic transducer, such as an EMAT, can be disposed within a downhole tubular, activated to induce one or more SH modes in the tubular, and the resulting waveforms monitored. Based on the measured results, some or all of the group velocity, phase velocity and frequency are obtainable for each wave modes monitored. Note, that neither SH0 frequency nor SH0 group velocity depend on tubular thickness. As such, measured results for the SH0 mode can be used to calibrate the thickness measurements done for nth mode (n>0). Moreover, the tubular thickness can be estimated by monitoring only the SH0 mode and a one additional mode. Table 1 below includes expressions for estimating tubular thickness based on measured wave frequency, group velocity, and phase velocity.

TABLE 1

| Measured Quantities | $f_n$ | $V_g^n$ | $V_p^n$ |
|---|---|---|---|
| $f_0$ | $\dfrac{0.5\lambda n}{\sqrt{(f_n/f_0)^2 - 1}}$ | $\dfrac{0.5\lambda n}{\sqrt{(f_0\lambda/V_g^n)^2 - 1}}$ | $\dfrac{0.5\lambda n}{\sqrt{(V_p^n/(f_0\lambda))^2 - 1}}$ |
| $V_s = V_g^0 = V_p^0$ | $\dfrac{0.5\lambda n}{\sqrt{(f_n\lambda/V_s)^2 - 1}}$ | $\dfrac{0.5\lambda n}{\sqrt{(V_s/V_g^n)^2 - 1}}$ | $\dfrac{0.5\lambda n}{\sqrt{(V_p^n/V_s)^2 - 1}}$ |
| $f_n$ | NA | $\dfrac{0.5\lambda n}{\sqrt{\lambda f_n/V_g^n - 1}}$ | NA |
| $V_g^n$ | $\dfrac{0.5\lambda n}{\sqrt{\lambda f_n/V_g^n - 1}}$ | NA | $\dfrac{0.5\lambda n}{\sqrt{V_p^n/V_g^n - 1}}$ |
| $V_p^n$ | NA | $\dfrac{0.5\lambda n}{\sqrt{V_p^n/V_g^n - 1}}$ | NA |

Based on the expressions in Table 1 it was determined that casing (or tubular) thickness is measurable based on results of a single nth mode. This is possible by measuring either group velocity and frequency, or group and phase velocities of the nth mode (n>0). It was additionally concluded that true thickness calculations require an accurate transducer wavelength. As such, a broad band signal should be used if the transducer lacks a well defined wavelength. Optionally, thickness calculations are possible by measuring values from two different SH modes. For example, the use of frequencies, phase or group velocities of SH modes m and n ($m \neq n$, $m>0$, $n>0$) leads to the following formulae:

$$d = 0.5\lambda \sqrt{\dfrac{(nV_g^n)^2 - (mV_g^m)^2}{(V_g^m)^2 - (V_g^n)^2}} \quad (5)$$

$$= 0.5\lambda \sqrt{\dfrac{(nV_p^m)^2 - (mV_p^n)^2}{(V_p^n)^2 - (V_p^m)^2}}$$

$$= 0.5\lambda \sqrt{\dfrac{(nf_m)^2 - (mf_n)^2}{f_n^2 - f_m^2}}$$

Higher SH mode waves typically exhibit a lower signal to noise ratio and attenuate more into cement than lower SH mode waves. Therefore, the expressions of Table 1 focus on the lower SH wave modes of SH0 and SH1. It was determined the transmitter to receiver close proximity is insufficient for higher wave mode separation and modes one and greater phase velocity exceeds shear velocity. Accordingly, the expressions in Table 1 having phase velocity were no longer considered leaving the formulae containing group velocities and frequencies. The remaining relationships are:

$$d_1 = \dfrac{0.5\lambda n}{\sqrt{(f_n/f_0)^2 - 1}}, \quad (6)$$

$$d_2 = \dfrac{0.5\lambda n}{\sqrt{(f_0\lambda/V_g^n)^2 - 1}}, \quad (7)$$

$$d_3 = \dfrac{0.5\lambda n}{\sqrt{(f_n\lambda/V_s)^2 - 1}}, \quad (8)$$

$$d_4 = \dfrac{0.5\lambda n}{\sqrt{(V_s/V_g^n)^2 - 1}}, \quad (9)$$

$$d_5 = \dfrac{0.5\lambda n}{\sqrt{\lambda f_n/V_g^n - 1}}, \quad (10)$$

where $d_i$ ($i=1, \ldots, 5$) are five different estimations of the thickness.

A downhole tool disposable in a cased wellbore has dimensions and a configuration dictated by the wellbore size and shape. These downhole tool dimensional constraints correspondingly restrict EMAT design to having up to about five rows of magnets. EMAT embodiments for use with the present method employ two, three or four rows of magnets. Tubular curvature also requires the magnet arrays for downhole EMATs be arranged in the same or similar curvature. During development of the method herein described, it was discovered that EMATs having five or fewer magnet rows in an array generated shear waves in tubulars with wavelengths unequal to twice the magnetic row width. This is a departure from traditional EMAT practice and theory where it was widely accepted that EMAT generated waves had a wavelength twice the magnetic row width. Thus, it was further determined that transducer wavelength λ cannot be assumed constant and independent of the casing thickness. It was discovered to be based on formula (4) as the ratio of $0^{th}$ mode group velocity and frequency:

$$\lambda = V_s/f_0 = V_g^0/f_0. \quad (11)$$

The wavelength λ of equation (11) is referred to herein as the "effective" wavelength and substituted in formulae (6) through (10) for casing thickness estimation.

EXAMPLE

Figure 4A:
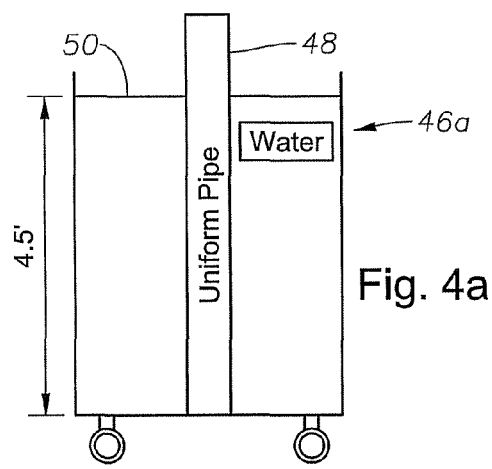
FIGS. 4a-4c depict test models.
Figure 4B:
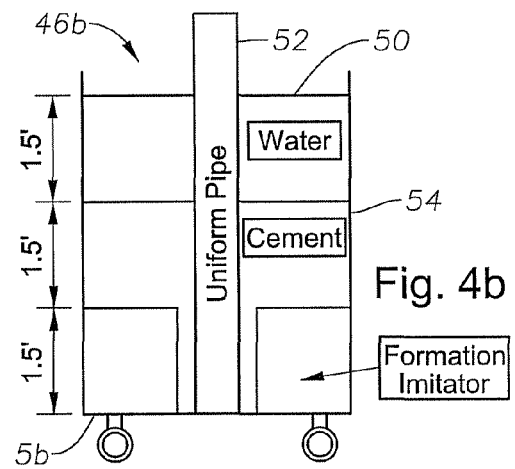
Figure 4C:
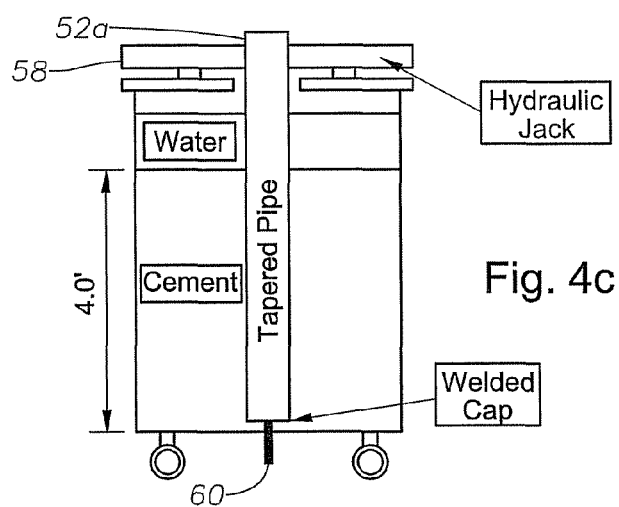

An SH probe configured similar to the tool 32 of FIG. 3 was tested in four different casing configurations using three different models. EMAT's were includes in the probe's transmitter and two receivers. Each EMAT comprised a magnet array strategically arranged so each magnet was bordered by an oppositely polarized magnet. The magnet array had three rows and five columns, where the rows were 0.25 inches in width. The three types of physical models of cemented pipe used in the experiments are schematically depicted in FIGS. 4a-4c. Details specifying the cement type, casing dimensions, and measured shear wave attenuation are provided in Table 2 below. FIG. 4a illustrates a test stand 46a used for Model 1 that simulates an un-cemented free pipe 48 partially extending into water 50. Test stand 46b, which was used for Model 2 and 3, is schematically depicted in FIG. 4b. Here a pipe 52 lower portion is anchored in cement 54 and extends upward through water 50. A formation imitator 56 surrounds the lower section of cement 54. Test stand 46c schematically represents Model 4, where a cemented casing 52a with varying thickness was analyzed. Also depicted with test stand 46c are a hydraulic jack 58 circumscribing the pipe 52a upper end and a welded cap 60 affixed on the pipe 52a lower end.

Using the models, the present method was investigated in free pipe and cemented along with its response to varying pipe thickness (in case of Model 4). It should be pointed out that Models 2, 3, and 4 each had a free pipe section at the top. The testing typically started the probe at each pipe bottom then, while activating the transmitter 36, the probe was pulled to the pipe upper end. Data was acquired while drawing the probe upward. The different models allowed analysis of casing with and without cement.

As shown in Table 2, the pipe thickness for Models 1, 2, and 3 was not performed independently. The measured value of the thickness for Model 4 is shown in Table 3. The measurements were done at 3 different distances from the bottom of the pipe for 3 different points around the circumference (120 degrees apart).

TABLE 3

| Distance from the bottom | 3 measured thickness values (120 degrees apart) | Average thickness |
|---|---|---|
| 3" | 7.41 mm (.292"), 7.70 mm (.303"), 8.03 mm (.316") | 7.72 mm (0.304") |
| 24" | 8.20 mm (.323"), 8.59 mm (.338"), 9.09 mm (.358") | 8.64 mm (0.340") |
| 44" | 8.03 mm (.316"), 9.09 mm (.358"), 10.16 mm (.40") | 9.09 mm (0.358") |

Figure 5:
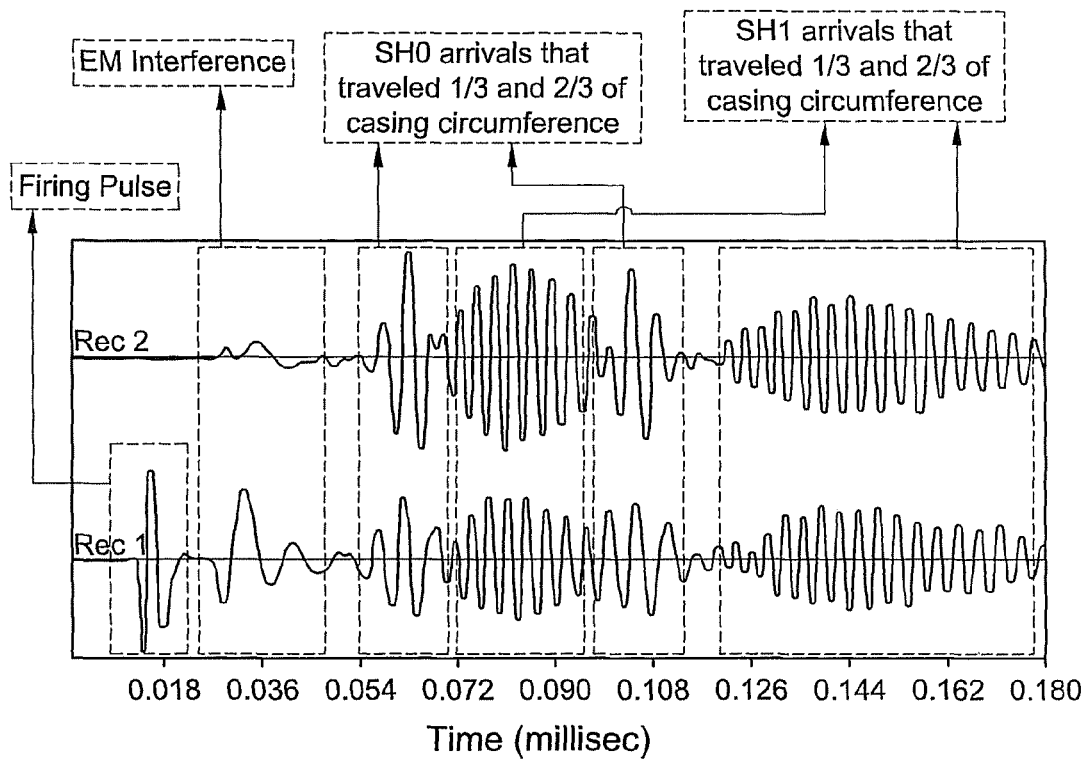
FIG. 5 graphically illustrates recorded SH0 and SH1 modes of an acoustic signal.

As discussed above, probe geometry traditionally dictated shear wave wavelength, i.e. λ=2× magnet row width (referred to herein as geometric wavelength). Thus each model's initial signal was assumed to induced a shear wave at the frequency corresponding to the geometric wavelength; which based on each model's EMAT was 0.5". The SH0 frequency at λ=0.5" is 252 kHz, for a typical steel shear velocity of 3200 m/sec based on formula (11). Since the signal contained only one sinusoidal cycle (due to testing system constraints), the actual acoustic energy input to the pipe was very broad banded and resulted in excitation of both SH0 and SH1 modes as can be seen in FIG. 5.

Figure 6:
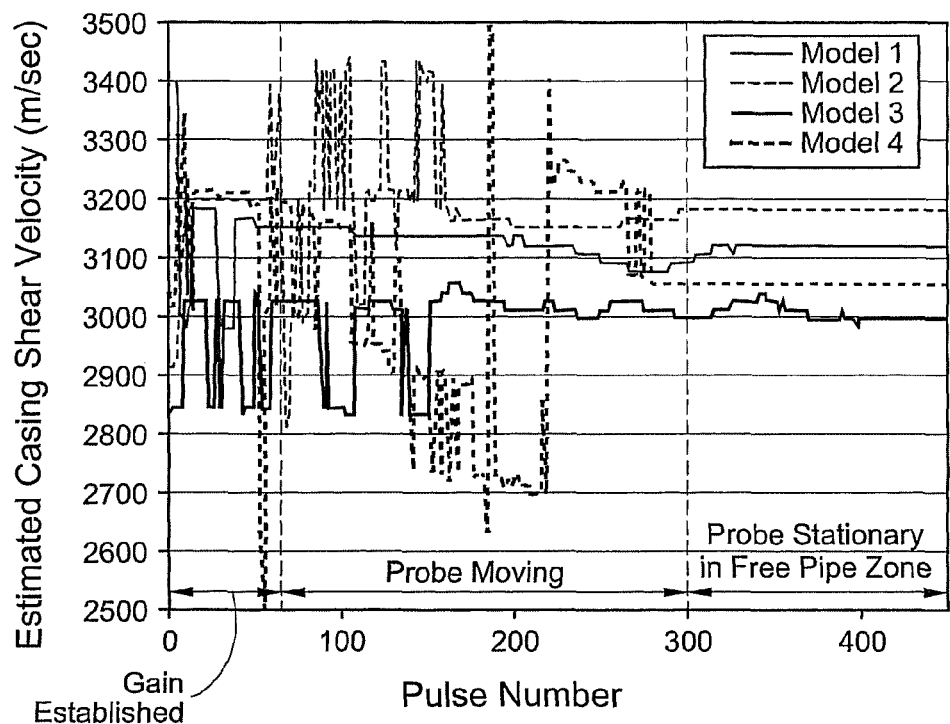
FIGS. 6 and 7 graphically represent estimated casing shear velocity for the test models of FIGS. 4a-4c.

SH0 mode group velocity calculations were performed in each of Models 1-4 using a constant distance between receivers calculated from the known pipe inner diameter. The calculations also included time of flight based on the maximum of cross-correlation function between the signals that traveled ⅓rd and ⅔rd of the circumference to different receivers. To improve the signal to noise ratio the data was filtered and running average of 8 signals was taken through the entire scan. FIG. 6 demonstrates casing shear velocity results of those calculations.

The scans done in the models are separated into three parts. In the first part the probe rests at the bottom of the model while the firing system establishes the gain, the second part consists of probe running through the length of the model while the third part was done in stationary probe conditions in the free pipe section. While some variation of shear velocity is possible throughout the casing length due to intrinsic stresses present in the pipe, its value was expected to be in the range from 3000 to 3200 m/sec. This range is seen in the free pipe section for all the models.

The data obtained in Model 1 (free pipe) demonstrates less variation when compared to the data in other models. Results from the cemented models include the finding that the shear

TABLE 2

| Model # | Type of cement | Casing thickness and ID | SH0 & SH1 cemented section's attenuation |
|---|---|---|---|
| Model 1 (FIG. 4a) | No cement (free pipe) | 7.75 mm (0.305") nominal thickness, 124.21 mm (4.89") ID | NA |
| Model 2 (FIG. 4b) | Extended slurry (14 ppg) | 7.75 mm (0.305") nominal thickness, 124.21 mm (4.89") ID | 23 dB/ft & 45 dB/ft |
| Model 3 (FIG. 4b) | Foamed cement (10 ppg) | 10.29 mm (0.405") nominal thickness, 119.13 mm (4.69") ID | 8 dB/ft & 15 dB/ft |
| Model 4 (FIG. 4c) | Extended slurry (14 ppg) | See Table 2 (for thickness), 119.13 mm (4.69") ID | 23 dB/ft & 45 dB/ft | velocity can be overestimated due to cycles skipping in the presence of very high attenuation. Shear velocity can be underestimated due to interactions from SH1 mode. The underestimation primarily occurs in the thicker casing because SH1 frequency decreases as thickness increases. FIG. 6 demonstrates that the SH0 mode was correctly identified in the data (time domain). Also demonstrated is the frequency corresponding to the central part of the signal can be used to optimize the firing sequence used for SH0 and SH1 modes.

The calculation of group velocity based on cross correlation of the signals that traveled $\frac{1}{3}^{rd}$ and $\frac{2}{3}^{rd}$ of pipe circumference was found to be difficult and unreliable in the cemented sections of the models. This was understood to be due in part to excessive signal attenuation. Additionally, in formulae (6) through (10), correctly estimating pipe thickness requires that both frequency and velocity variations around the circumference be measured along the same interval. Because of these issues the group velocity estimations presented further are based on the calculation of time of flight between the transmitter and nearest receiver. Since the exact moment of $t_0$, the group velocity excitation start at the transmitter, was not known, it was calibrated based on group velocities estimations in free pipe sections of each model for SH0 and SH1 modes separately.

Figure 7:
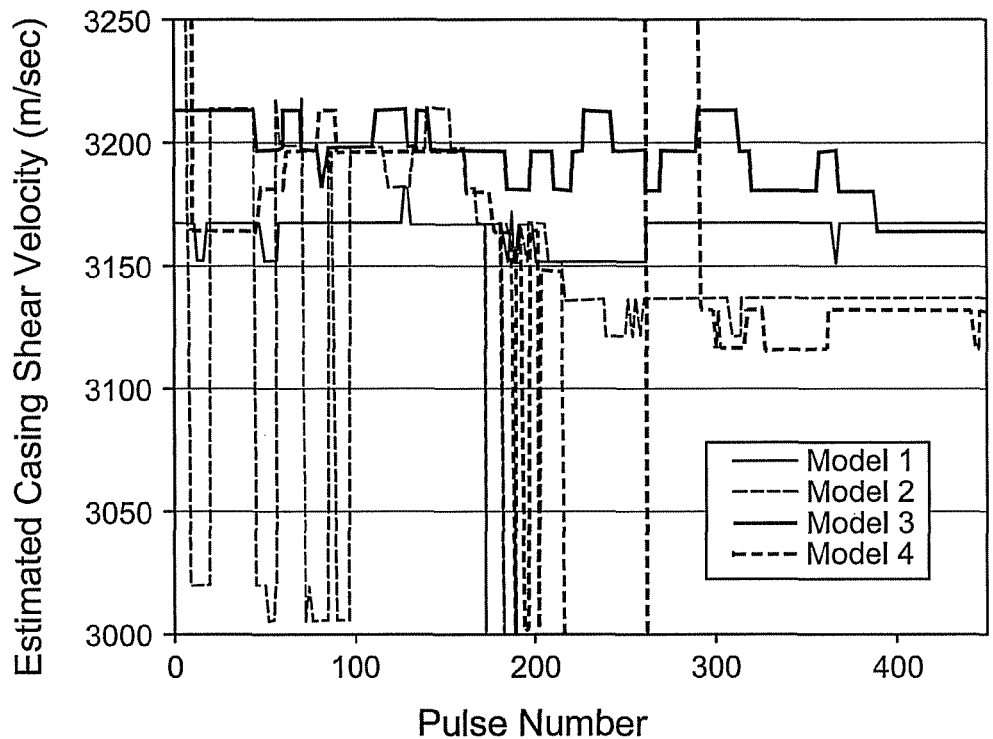

The results of calculations of the group velocities of SH0 mode are presented in FIG. 7. As can be seen from this figure Models 1 through 4 show the constant estimate value of the shear velocity through the whole length of the pipe. It should be noted that the curves presented here vary less than the curves in FIG. 6. Also, the presence of cement (pulses 1 through 180) only slightly affects the velocity estimations in the case of Model 2. In the other models, cement was not found to affect this measurement. As demonstrated by data obtained in Models 2 and 4, the cement-fluid interface was found to cause a sudden drop in SH0 mode apparent velocity close to pulse number 200.

Figure 8:
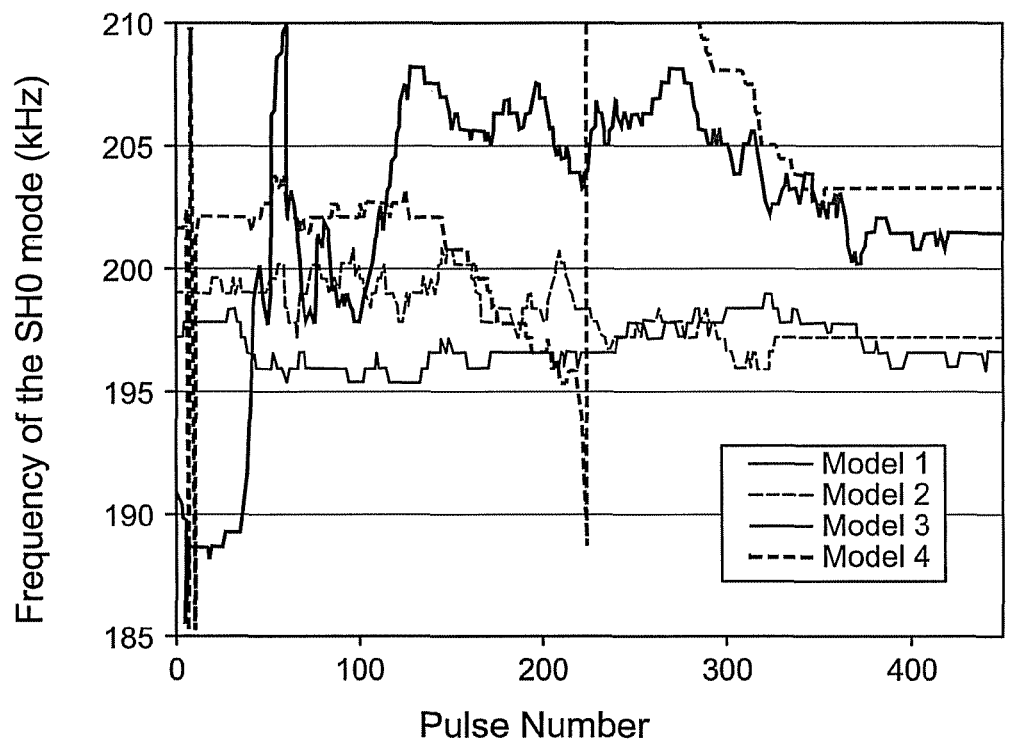
FIG. 8 is a graph of SH0 mode for the test models of FIGS. 4a-4c.
Figure 9:
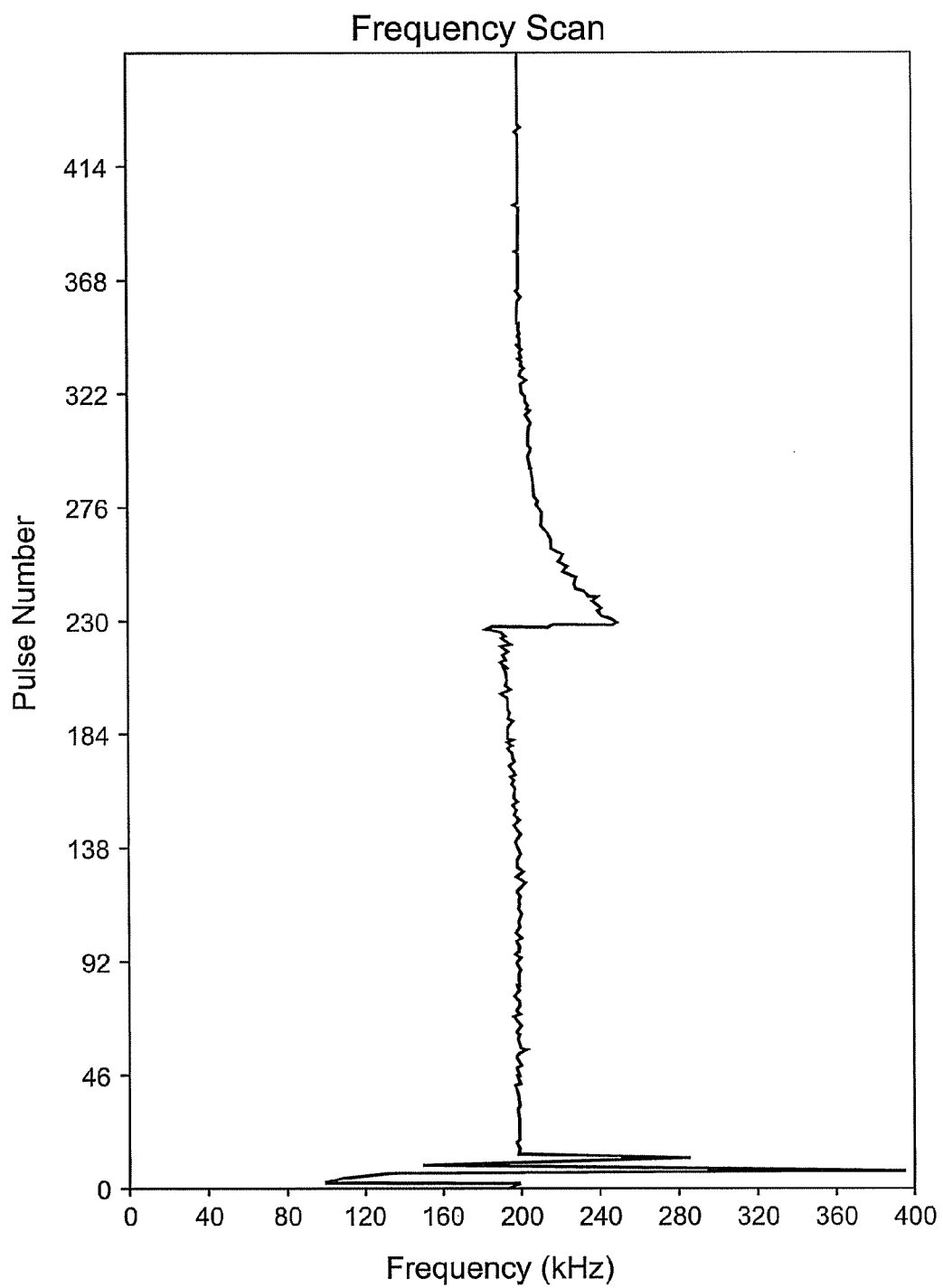
FIG. 9 is a frequency scan of a test of the model of FIG. 4c.

As shown in FIG. 8, the presence of cement-fluid interface using the SH0 mode frequency plot was only detected for Model 4. The SH0 mode frequencies obtained from Models 1 through 3 varied only slightly through the scan while the Model 4 SH0 mode frequency had a large spike when entering the free pipe section. This spike was also demonstrated in FIG. 9, that shows VDL type of presentation for the frequency of SH0 mode in Model 4.

Figure 10:
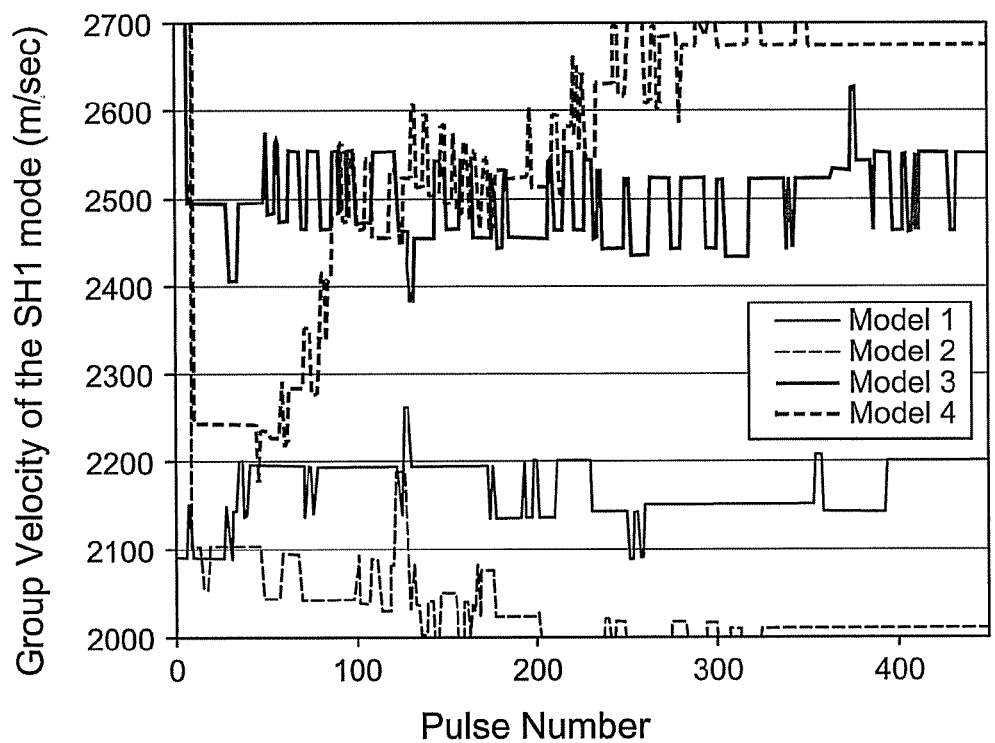
FIGS. 10-12 include graphs respectively representing SH1 group velocity, SH1 frequency, and effective signal wavelength for the models of FIGS. 4a-4c.

FIG. 10 shows the estimations of the SH1 velocity in different models. In accordance with formula (3), the Model 3 SH1 group velocity (nominal casing thickness of 10.27 mm) is higher than in Model 1 (nominal casing thickness of 7.75 mm). The SH1 group velocity in these models varies only slightly through the length of the scan. This is likely due to the constant casing thickness and the Model 1 free pipe condition and very low attenuation through the Model 3 cemented section. The SH1 group velocity in Model 4 shows a general trend upward in accordance with formula (3). At the start of the scan the Model 4 SH1 group velocity approximates Model 1 values and approximate Model 3 values at the end of the scan. Note, at its bottom portion the Model 4 casing thickness is similar to the Model 1 casing thickness, and at its top, the Model 4 casing thickness is similar to the Model 3 casing thickness. The Model 4 scan ended proximate the hydraulic jack (see FIG. 4c). It is believed the additional mass attached to the casing pushes the group velocity higher at the end of the scan. The values obtained in Model 2 are similar to the values obtained in Model 1 since casing in both models has similar thickness.

Figure 11:
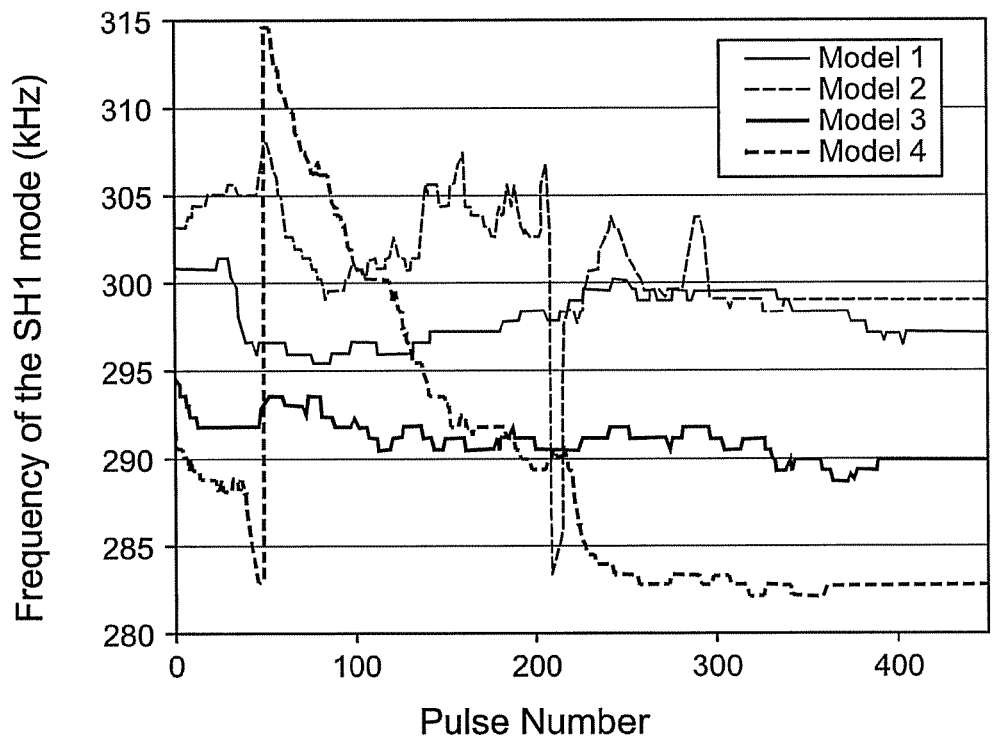

FIG. 11 graphically displays the SH1 mode frequency for different models. As predicted by formula (1) (SH1 frequency is higher for thinner casing), a correlation between the casing thickness and frequency can be observed in FIG. 1. A low frequency reading at the beginning of the scan (before the probe was put in motion) in Model 4 can be explained by the presence of a very thick plate at the bottom of this model. The scan in Model 4 ended close to the hydraulic jack, here the frequency was lower than at the start of the scan. A sudden drop of frequency in Model 2 data corresponds with the probe was crossing the cement-water boundary.

Figure 12:
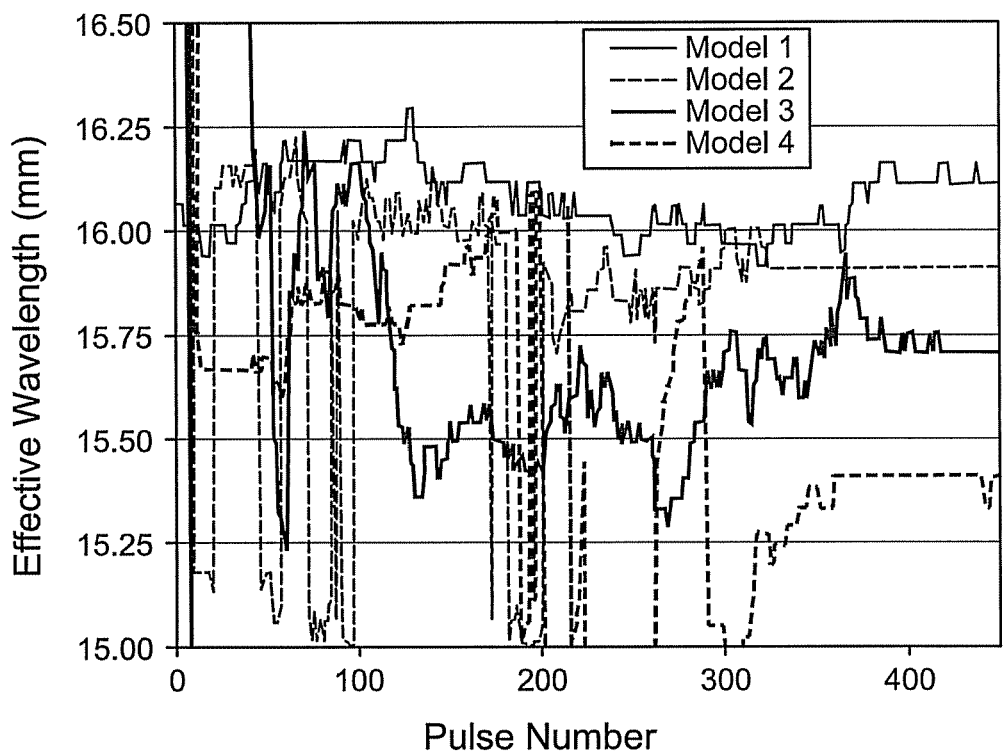
Figure 13:
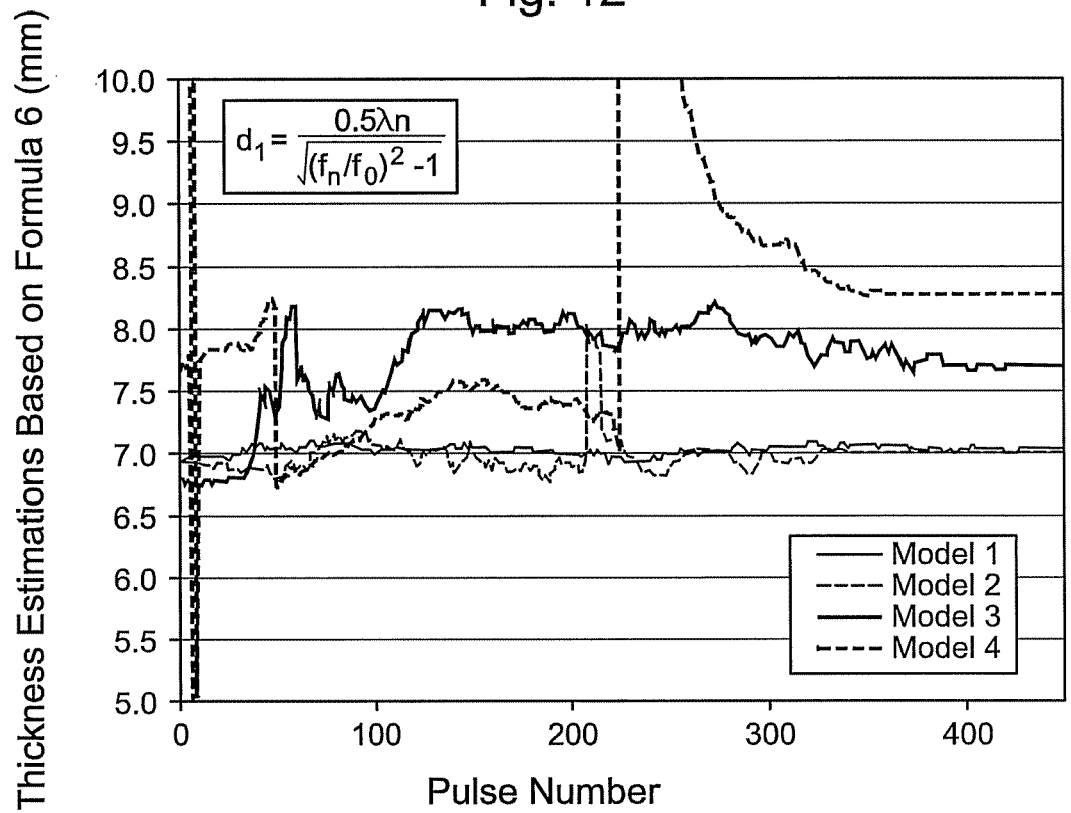
FIGS. 13-17 include graphs of casing thickness estimates of the models of FIGS. 4a-4c.
Figure 14:
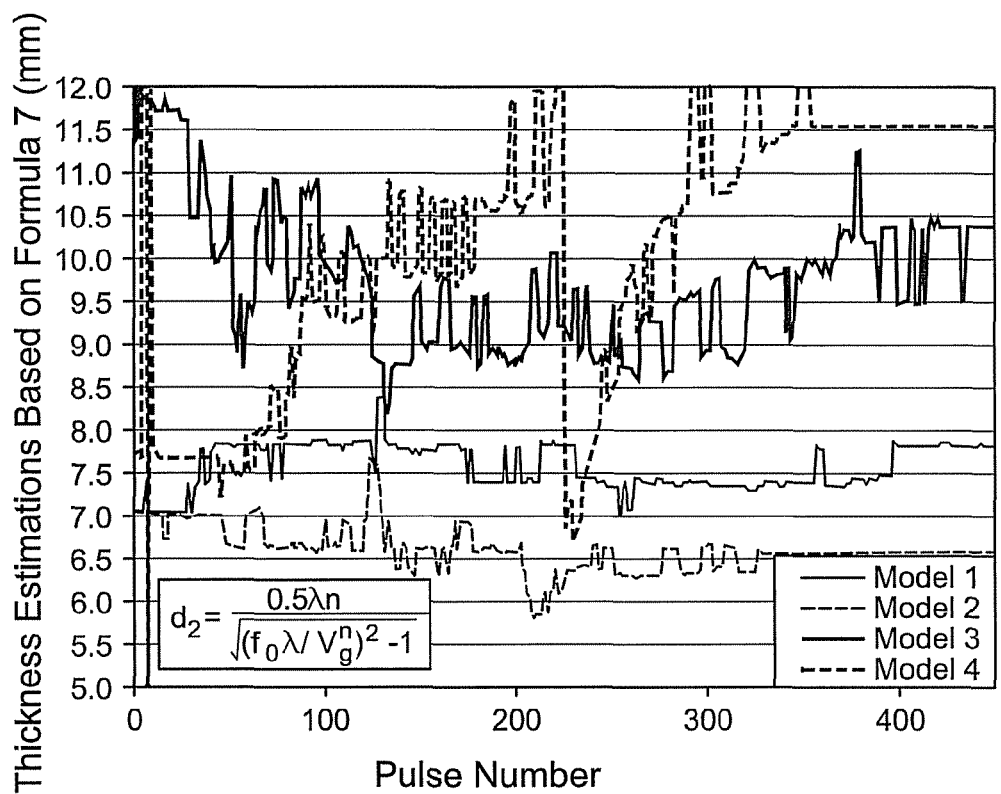
Figure 15:
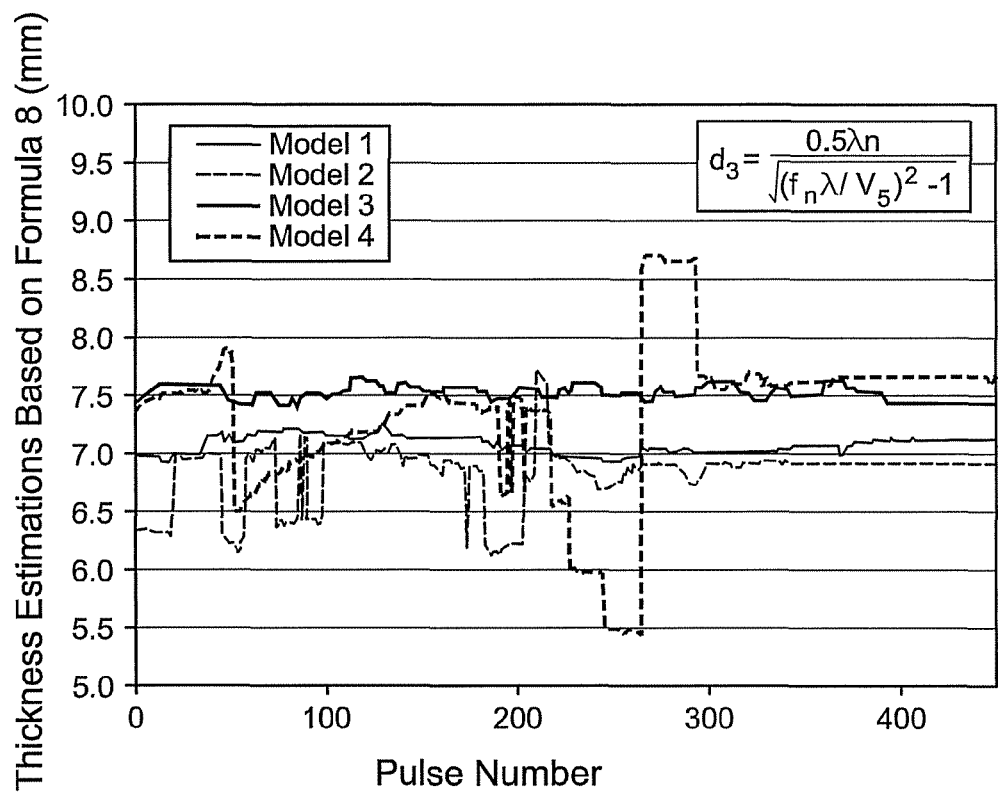
Figure 16:
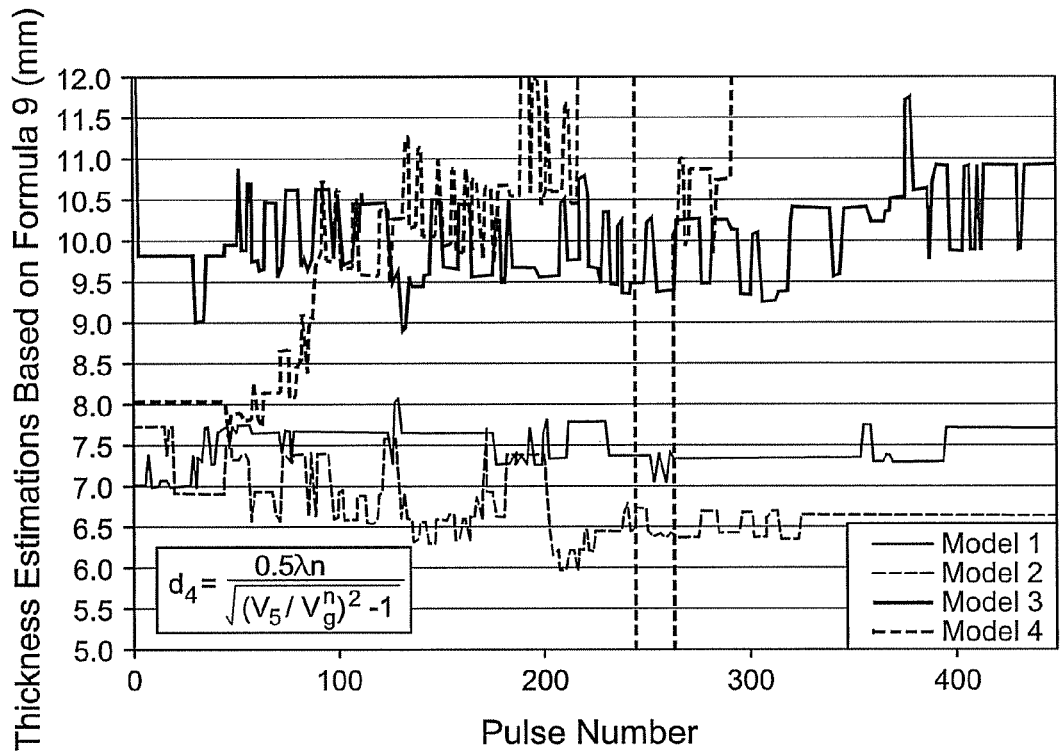
Figure 17:
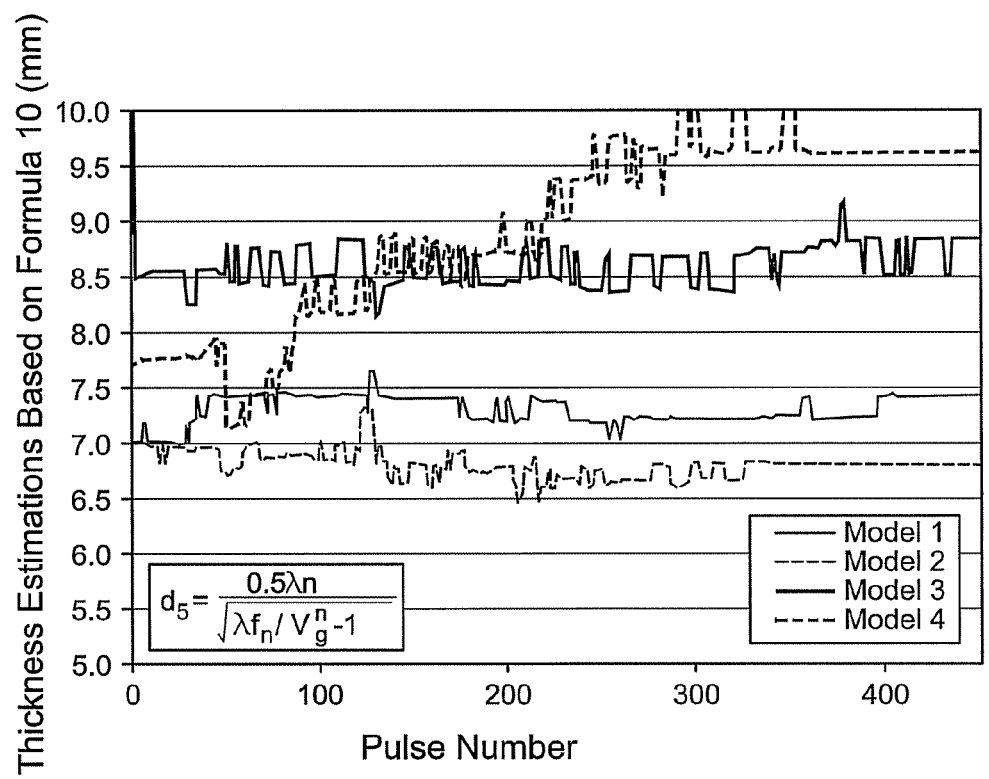

With reference now to FIG. 12, probe calibration results for the models are graphically displayed. As discussed above, calibration signals were fired over a frequency range into the model and monitored. The frequency of the monitored signal having the highest signal to noise ratio was identified. From the calibration results and formula (11) the effective wavelength of the probe was determined to be 16 mm, which is almost 26% greater than the expected geometric wavelength of 12.7 mm (0.5 inches).

FIGS. 13 through 17 are plots illustrating a calculated casing thickness versus signal pulse number. The thickness values presented in the plots of FIGS. 13 through 17 were calculated from formulae (6) through (10) respectively. The figures indicate each model's thickness trend was predicted by these formulae. The relative ratio between the absolute values of thicknesses was also correctly estimated by the formulae. Formula (9), which uses the group velocities of modes SH0 and SH1 (FIG. 16) was deemed the most accurate estimator of thickness in terms of absolute values. This conclusion is based on comparison of the thickness estimations in FIGS. 13 through 17 with the thickness data presented in Tables 2 and 3. Accordingly, calculating tubular thickness based on an effective wavelength rather than a geometric wavelength provides a substantially more accurate thickness value.

Figure 18:
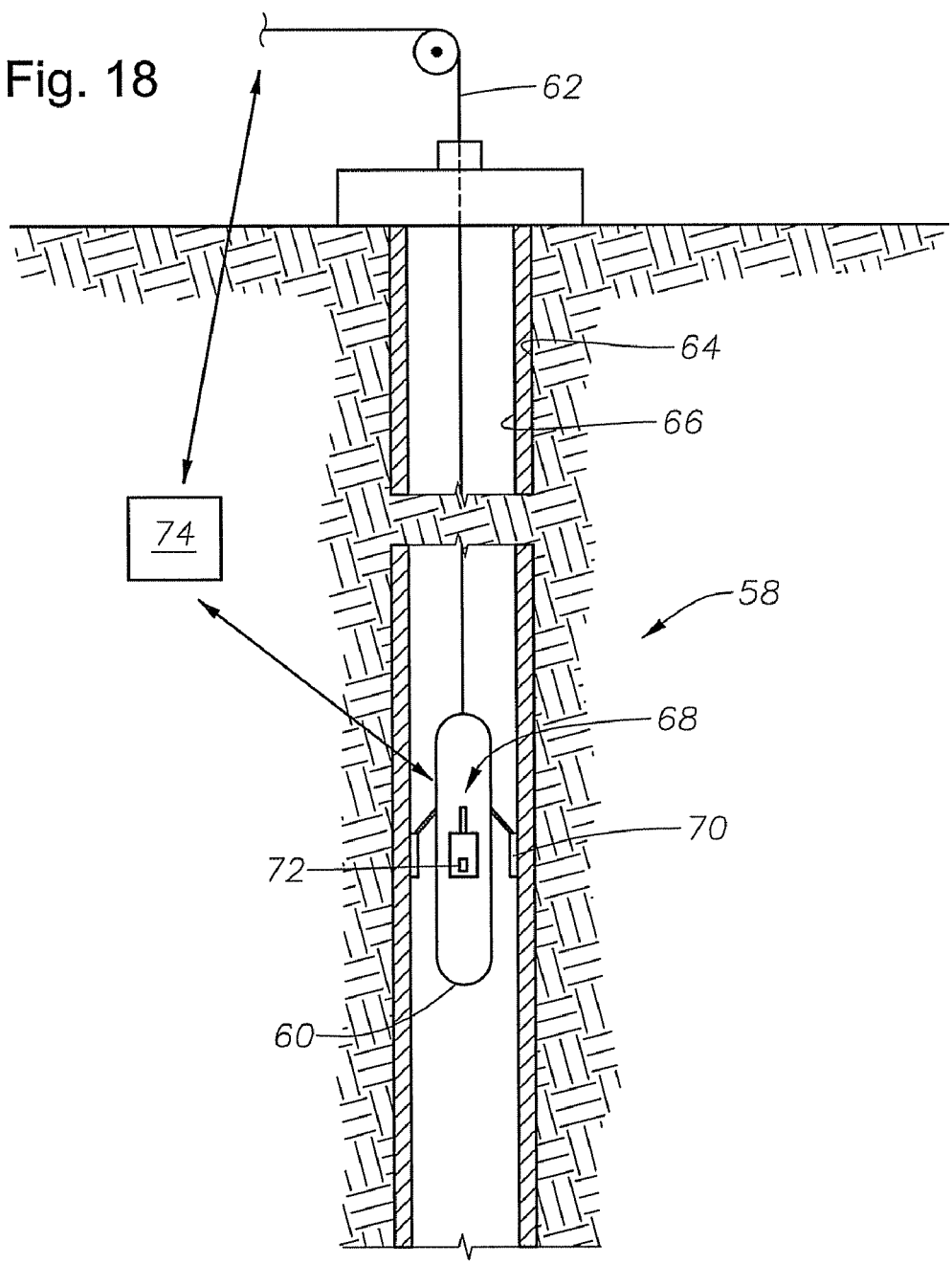
FIG. 18 is a partial sectional view of an embodiment of a logging system.

An example of a logging system employing an embodiment of the method herein described is illustrated in a side partial sectional view in FIG. 18. The system illustrated is a downhole logging system 58 comprising a downhole tool 60 or sonde attached to a wireline 62 and disposed in a wellbore 64. The tool 60 is shown gathering information from casing 66 that lines the wellbore 64. Sensor arms 68 pivotingly attached to the tool 60 housing include pads 70 secured to the arms' 68 ends. Each pad 70 includes a transducer 72 thereon, the transducer 72 may be an acoustic transmitter, receiver, or both transmit and receive. Example transducers 72 include an EMAT, piezoelectric, wedge, and laser.

Pivoting the arms 68 extends the pads 70 outward from the tool 60 housing and toward the casing 66. Disposing a pad 70 outward places its corresponding transducer 72 proximate the casing 66, thereby facilitating interaction between the transducer 72 and casing 66. In the embodiment of FIG. 18, three pads 70 with transducers 72 are illustrated, however other embodiments exist that include two, four, five, or more pads, each pad with one or more transducers. In each embodiment at least one transducer 72 is a transmitter configured to transmit a signal that propagates through the casing 66, such as an acoustic signal, and at least one transducer 72 is a receiver configured to receive the signal transmitted through the casing 66. Through the casing includes a signal propagating around the casing 66 circumference, along the casing 66 length, or directly through the casing 66 wall. Moreover, the logging system 58 is not limited to logging casing, but can monitor and analyze other tubulars as well. Signals received by the receivers can be analyzed using the above described method to determine casing 66 thickness.

A controller 74 may optionally be included with the system 58, where the controller 74 communicates through the wireline 62 to the tool 60 or directly with the tool 60 independent of the wireline 62. The controller 74 may be disposed on surface or combined with the tool 60 and inside its housing. The controller 74 may be a microprocessor or other information handling system. The controller 74 can be used to provide commands to the tool 60 and its components, and/or receive data from the tool 60, such as data received by its receiver transducers 72. The controller 74 can also be configured to determine casing 66 thickness using the method above described or some other method.

The present invention described herein, therefore, is well adapted to carry out the objects and attain the ends and advantages mentioned, as well as others inherent therein. While a presently preferred embodiment of the invention has been given for purposes of disclosure, numerous changes exist in the details of procedures for accomplishing the desired results. For example, the inverse of the time for a signal to travel between two transducers, that are a known distance apart, may be used as an alternative manner to measure signal velocity. These and other similar modifications will readily suggest themselves to those skilled in the art, and are intended to be encompassed within the spirit of the present invention disclosed herein and the scope of the appended claims.

What is claimed is:

1. A method of evaluating a tubular used in hydrocarbon production, the method comprising:
    inducing a shear wave SH0 mode and a shear wave SH1 mode in the tubular;
    measuring the SH0 mode group velocity;
    measuring the SH1 mode group velocity ($V_g$);
    assigning the measured SH0 mode group velocity as the tubular material shear velocity ($V_s$);
    estimating a shear wave wavelength $\lambda$ from the ratio of SH0 mode frequency ($f_o$) and the measured SH0 group velocity; and
    estimating the tubular thickness (d) from the estimated shear wave wavelength $\lambda$.

2. The method of claim 1, further comprising estimating the tubular thickness (d) using the relationship: $d=0.5\lambda/((V_s/V_g)^2-1)^{1/2})$.

3. The method of claim 1, further comprising inducing additional shear waves in the tubular over a range of frequencies, monitoring the shear waves' propagation in the tubular, evaluating the signal to noise ratio of monitored waves at selected frequencies, adjusting the tool to induce shear waves at the selected frequency having the largest signal to noise ratio.

4. The method of claim 3 further comprising inducing a shear wave at the selected frequency having the largest signal to noise ratio, measuring the SH0 mode group velocity, and re-estimating the shear wave wavelength $\lambda$ based on the measured SH0 mode group velocity.

5. The method of claim 1, wherein the tubular comprises an annular member selected from the list consisting of casing lining a wellbore and production tubing disposed in a wellbore.

6. The method of claim 1, further comprising inserting into the tubular a tool having an electromagnetic acoustic transducer (EMAT) that includes a magnet array having at least three rows of magnets.

7. The method of claim 6 wherein the magnetic rows are aligned substantially parallel with the tubular axis.

8. The method of claim 6, wherein the EMAT lies in a plane substantially perpendicular to the tubular axis, and wherein the shear wave is monitored within the plane at about 120° along the tubular circumference away from the EMAT.

9. The method of claim 6, wherein the EMAT lies in a plane substantially perpendicular to the tubular axis, and wherein the shear wave is monitored within the plane at about 240° along the tubular circumference away from the EMAT.

10. The method of claim 6, wherein the magnet array comprises up to five rows of magnets.

* * * * *